United States Patent
Premachandran et al.

(10) Patent No.: US 11,224,222 B2
(45) Date of Patent: Jan. 18, 2022

(54) SYNERGISTIC COMPOSITIONS OF DEHYDROACETIC ACID AND METHODS FOR REDUCING YELLOWING IN VARIOUS END-USER COMPOSITIONS

(71) Applicant: ISP Investments LLC, Wilmington, DE (US)

(72) Inventors: Raman Premachandran, Saddle Brook, NJ (US); Kalpa Metha, Raritan, NJ (US); Jyoti Gupta, Basking Ridge, NJ (US); Najeeb H. Hakimi, Edison, NJ (US); Karen W Winkowski, Springfield, NJ (US)

(73) Assignee: ISP Investments LLC, Wilmington, DE (US)

( * ) Notice: Subject to any disclaimer, the term of this patent is extended or adjusted under 35 U.S.C. 154(b) by 0 days.

(21) Appl. No.: 15/561,222

(22) PCT Filed: Mar. 25, 2016

(86) PCT No.: PCT/US2016/024153
§ 371 (c)(1),
(2) Date: Sep. 26, 2017

(87) PCT Pub. No.: WO2016/154511
PCT Pub. Date: Sep. 29, 2016

(65) Prior Publication Data
US 2018/0055048 A1    Mar. 1, 2018

Related U.S. Application Data

(60) Provisional application No. 62/138,490, filed on Mar. 26, 2015.

(51) Int. Cl.
*A61K 8/35* (2006.01)
*A01N 43/16* (2006.01)
(Continued)

(52) U.S. Cl.
CPC ............ *A01N 43/16* (2013.01); *A01N 25/02* (2013.01); *A61K 8/35* (2013.01); *A61K 8/498* (2013.01);
(Continued)

(58) Field of Classification Search
CPC ........................................................ A61K 8/35
See application file for complete search history.

(56) References Cited

U.S. PATENT DOCUMENTS

| 5,814,343 A | 9/1998 | Jones et al. |
| 2008/0234173 A1* | 9/2008 | Warr et al. |

(Continued)

FOREIGN PATENT DOCUMENTS

WO    WO2014135650 A1    9/2014

OTHER PUBLICATIONS

International Search Report, PCT/US2016024153 published on Sep. 29, 2016.

*Primary Examiner* — Benjamin J Packard
(74) *Attorney, Agent, or Firm* — William J. Davis; Nathalie Tietcheu

(57) ABSTRACT

What is described herein is a stable and reduced-yellowing/non-yellowing synergistic preservative composition comprising: (i) about 0.1 wt. % to about 40 wt. % of dehydroacetic acid (DHA); and about 0.1 wt. % to about 99.9 wt. % of at least one aprotic solvent. Also described herein are aqueous and non-aqueous based preservative compositions for various end-user applications, and processes for preparing and using such compositions to reduce yellowing of DHA when added to the end-user applications.

19 Claims, 2 Drawing Sheets

(51) Int. Cl.
  *A61Q 19/00*  (2006.01)
  *A61K 8/49*   (2006.01)
  *A01N 25/02*  (2006.01)
  *A61Q 5/02*   (2006.01)

(52) U.S. Cl.
  CPC .............. *A61K 8/4973* (2013.01); *A61Q 5/02* (2013.01); *A61Q 19/00* (2013.01); *A61K 2800/524* (2013.01)

(56) References Cited

U.S. PATENT DOCUMENTS

| | | |
|---|---|---|
| 2008/0299220 A1 | 12/2008 | Tamarkin et al. |
| 2012/0282195 A1* | 11/2012 | Florence .............. A61K 8/9794 424/59 |
| 2013/0058883 A1* | 3/2013 | Kergosien ................ A61K 8/31 424/70.7 |
| 2013/0058885 A1* | 3/2013 | Burt et al. |
| 2013/0115315 A1 | 5/2013 | Derkx |
| 2014/0038933 A1 | 2/2014 | Polson, et al. |

* cited by examiner

SYNERGISTIC COMPOSITIONS OF DEHYDROACETIC ACID AND METHODS FOR REDUCING YELLOWING IN VARIOUS END-USER COMPOSITIONS

FIELD OF THE INVENTION

The present application relates to a method for reducing and/or preventing yellowing of Dehydroacetic Acid (DHA). More particularly, there is disclosed a stable, synergistic and non-yellowing/reduced-yellowing preservative composition comprising dehydroacetic acid and at least one aprotic solvent, and its use in various aqueous and non-aqueous based end-user applications.

BACKGROUND OF THE INVENTION

Preservatives or preservative systems are employed in various industrial applications including personal care, household, coatings, metalworking fluids, paper, wood, plastics, disinfection, cosmetics, toiletry, pharmaceuticals, food, beverages, oral care, paints, or water treatment to overcome the problems of mildew, mold, fungi, bacterial based microbial contamination.

Particularly, personal care, pharmaceuticals, food, beverages, nutrition care products fragrance products, cosmeceuticals, nutraceuticals, cosmetics, treatment, skin care and anti-aging products usually incorporate ingredients that support microbial growth and proliferation, and therefore, these products require significant amount of preservatives as they directly affect consumers. Additionally, regardless of their use, these products in general include an aqueous medium as one important component. This aqueous phase facilitates a medium in which microorganisms can survive and/or proliferate. Thus, these products by their very nature create an environment and viable medium for the proliferation of microbial organisms. Without the addition of some preservative agent, these types of products are susceptible to microbial contamination and proliferation.

The personal care or cosmetic composition and stability are of particular relevance in our daily life as these products can be applied to the human body for the purpose of cleansing, beautifying, promoting attractiveness or altering appearance. Therefore, antimicrobial chemicals that prevent microorganisms from growing play a crucial role. These personal care products are very sophisticated and diverse in formulation. They often include a variety of natural and/or synthetic ingredients used to fulfill the aesthetic desires of the customer. Unfortunately, these ingredients also provide pH, moisture, and nutritional conditions that support microbial growth. Due to this potential vulnerability, many personal care products employ natural or synthesized preservatives to prevent spoilage.

Accordingly, a preservative can be added to such products at the time of manufacturing in order to protect the product against microbial contamination in the long term. The particular choice of type and level of the preservative is typically made by the formulator based upon a number of factors including, for example, the microbiological requirements of the product, cost, the pH of the product, compatibility with the other formulation ingredients and regulatory restrictions. A guide to the factors used in preservative selection and testing can be found in "Cosmetic and Drug Preservation, Vol. I, Principles and Practice", published by Marcel Dekker Inc.

However, in the recent past, the demand for natural consumer products is of great importance across the globe. Such natural sector has become one of the fastest growing in the North American personal care and cosmetics based industrial segments. Further it is projected that the healthy market growth rates for natural and organic products would increase for cosmetic and toiletry products in the years to come. The demand for such natural products plays direct role in contributing health benefits for the consumers and environmental benefits for the society, and these products would fall into any one of the following categories including: natural, green, organic, sustainable, holistic, bio-degradable, nature-identical, earth-friendly, regulatory-friendly, environmentally safe, preservative-free, and non-toxic.

The demand and importance of nature based products has provoked many formulators and customers to move away from traditional preservatives or preservative systems chiefly due to current stringent regulatory norms applicable across the globe. Such traditional preservatives include parabens, triclosan, isothiazolinones, quaternary ammonium compounds, formaldehydes & formaldehyde-donors, carbamates, IPBC, chlorophenisin. According to current regulatory guidelines, the permitted use levels of traditional preservatives are not capable of preserving end-user product. The strong negative consumer perception about these preservative agents drives the need for new preservatives or preservative systems.

Dehydroacetic acid (DHA) is a green, natural and sustainable preservative, duly approved by regulatory certification bodies, for example, Natural Products Association, Oasis, EcoCert, NaTrue, and Soil Association. Further, DHA is compatible with a wide range of skin care compositions and capable of delivering good efficacy in a pH range of 3 to 7, which is an ideal range for most skin care applications. But one significant problem encountered in the manufacture of finished compositions or end-user based formulations containing DHA is that such formulations have discoloration with time, temperature, and/or interaction with associated ingredients caused partly by DHA which turns yellow in color from its white colorless transparent nature. Such yellow coloration is undesirable for aesthetic reasons, as well as functional reasons relating to unwanted color in the resulting end-user based compositions. Specifically, skin care products employ DHA as their preferred preservative due its Eco-certified and natural nature; however, it is limited to pigmented formulation due to such discolaration. The aesthetics of end-user products are very important and formulators of such products go to great length to achieve such unique color effects of end-user products, and therefore any reason or fellow ingredient which causes the composition to differ from a desired white or colorless shade may make the developer task very difficult. Particularly, attempts to employ DHA as an anti microbial agent in end-user products create unwanted yellow color and adversely affect the color of the formulated product or change the anticipated color of the finished end-user product. As a result, this undesired color makes the formulations undesirable for the desired usage.

DHA is a significantly unstable molecule and undergoes hydrolysis in aqueous and non-aqueous based end-user products comprising polar or protic solvents such as water, ethanol, methanol, propanol, etc. The extent of discoloration of DHA varies according to the amount of protic solvent and/or DHA present in the non-aqueous and aqueous products respectively. Additionally, the intensity of yellow coloration of DHA upon hydrolysis may vary depending on exposure to Ultra-Violet (UV) light or exposure to heat or time lapsed on storage. Applicants determined that during hydrolysis of DHA, it generates oxygen centered or carbon centered free radicals which can undergo oxidative or reductive coupling to form UV absorbing compounds or impurities (trace level with high Epsilon) having unique chromophoric structures which are responsible for the formation of yellow coloration of DHA present in any protic solvent or aqueous/non-aqueous based end-user products comprising protic solvents and DHA at different concentration levels. The non-limiting chromophores derived during hydrolysis of DHA, include, but are not limited to, 1-(2,4-dihydroxy-3-methylphenyl)acetone, 2,5-dimethyl-7-hydroxy chromone, 3,5-dihydroxy toluene, 3,5-dimethyl phenol, 2,4,6-hepatnetrione, 2-acetyl-4,5-dimethyl phenol, 2,6-dimethyl-4H-pyran-4-one, 3,3,5-trimethyl-2-cyclohexen-1-one, 2,6-dimethyl-4H-pyran-4-one, 2-acetyl-4,5-dimethyl phenol, 4,5,7-trimethyl coumarin, 2,4-dimethyl-7-hydroxy chromone, 3,5-dimethyl phenol, and/or 3,3,5-trimethyl-2-cyclohexen-1-one.

US Publication No. 20120015986 assigned to Larry Kent Hall et al discloses a method for preventing discoloration of pyrithione-containing materials, in particular plastic materials or other material such as paints, coatings, adhesives or textiles which are exposed to an outdoor environment. The method is suited for preventing discoloration of other pyrithione-containing materials such as personal care compositions like shampoos. A discoloration inhibitor that includes dehydroacetic acid or a salt thereof is added to the pyrithione-containing material. The discoloration is prevented without the addition of a cyclic organic phosphoric acid ester or an organic phosphite. Use of the discoloration inhibitor does not interfere with the antimicrobial effect of the pyrithione.

U.S. Pat. No. 6,096,122 discloses a process for inhibiting the formation of discoloration in an aqueous composition selected from the group consisting of water-based paint, adhesive, caulk and sealant compositions, and combinations thereof, wherein the discoloration is caused by the presence of ferric ion or cupric ion together with pyrithione in the composition. The process comprises contacting the composition with a discoloration-inhibiting amount of a zinc compound selected from the group consisting of zinc salts of organic acids, zinc salts of inorganic acids, zinc hydroxide, zinc oxide, and combinations thereof. Also disclosed is an aqueous antimicrobial composition protected against discoloration attributable to the presence of ferric ion or cupric ion therein.

WO2014022369A1 assigned to Arch Chemicals discloses a method of reducing discoloration of compositions containing pyrithione compounds by addition of pyranone compounds and further to a composition containing a pyrithione compound, a pyranone compound and a co-chelator (preferably HEDP, EDTA and their salts or mixtures thereof).

JP2047371A assigned to Kyoeisha Chemical discloses a composition to be applied to a textile product to impart the textile with excellent softness and stretchability without causing the yellowing and discoloration of the fiber by using specific silicone oil as a main component. The composition exhibits excellent softness and stretchability and low thermal yellowing tendency compared with conventional softening agent. The composition may contain ethylene carbonate and propylene carbonate as one of its ingredients.

WO2012068455A1 discloses an aqueous, stable, highly-concentrated preservative composition comprising (i) about 5 to 50 wt % of a dehydroacetic acid (DHA) or a salt thereof; (ii) about 1 to 20 wt % of a 2-methyl-4-isothiazolin-3-one (MIT); (iii) about 0.1 to 10 wt % of at least one block copolymer; (iv) optionally, about 0.01 to 5.0 wt % of at least one sulfosuccinate surfactant; (v) optionally, about 0.01 to 5.0 wt % of at least one sequestering agent; and (vi) optionally, about 0.01 to 5.0 wt % of one or more additives. Also disclosed is a process for preparing said preservative composition.

There remains a need for a color-stable or non-yellowing/reduced-yellowing DHA to address the necessity of eco-friendly, natural and regulatory complying preservative for various end-user applications. Accordingly, it is an objective of the present application to provide a stable, synergistic and non-yellowing/reduced-yellowing DHA which is capable of retaining its natural color when added to aqueous or non-aqueous based end-user products.

SUMMARY OF THE INVENTION

The present application provides a stable, synergistic, reduced-yellowing and/or non-yellowing DHA which is capable of retaining its natural color when added to the aqueous or non-aqueous based end-user products.

The present application also provides a stable and non-yellowing/reduced-yellowing synergistic preservative composition comprising: (i) about 0.1 wt. % to about 40 wt. % of dehydroacetic acid (DHA); and about 0.1 wt. % to about 99.9 wt. % of at least one aprotic solvent.

The present application further provides a synergistic preservative composition of DHA, particularly in combination with desired aprotic solvents, and wherein, the DHA is solubilized in the aprotic solvents. The contribution of synergism by aprotic solvents allows employing significantly lesser amounts of DHA than required without the combination of such aprotic solvents. Therefore, the lesser amount of DHA employed capable of generating lower yellow intensity when employed in end-user products.

Another aspect of the present application is that the preservative composition is capable of inhibiting or killing *Candida tropicalis, Candida albicans, Hansenula anomala, Saccharomyces cerevisiae, Torulaspora delbreuckii, Zygosaccharomyces bailii, Zygosaccharomyces rouxii, Bacillus subtilis, Bacillus cereus, Staphylococcus aureus, Staphylococus epidermidis, Escherichia coli, Salmonella typhimurium, Salmonella enteritidis, Pseudomonas aeruginosa, Aspergillus niger, Aspergillus flavus, Penicillium islandicum, Penicillium citrinum, Penicillium chrysogenum, Fusarium oxysporum, Fusarium graminearum, Fusarium solani, Alternaria alternata, Aspergillus brasiliensis, Burkhodelia cepacia, Enterobacter aerogenes, Enterobacter cloacae, Enterobacter gergoviae, Klebsiella pneumoniae, Proteus vulgaris, Pseudomonas fluorescens, Pseudomonas putida, Penicillium pinophilum* and/or *Mucor racemosus*.

The preservative compositions of this invention can be employed in various aqueous and non-aqueous based end-user applications comprising cosmetic products, toiletry products, personal care products, oral care products, skin care products, hair care products, household & cleaning products, industrial and institutional cleaning products, disinfecting products, contact lens, enzyme based formulations, wound care, sanitary products, agricultural compositions, textile industries, coating industries and/or laundry products. The preservative composition can be delivered as an emulsion, microemulsion, nanoemulsion, solution, dispersion, suspension, complex coacervate or concentrate and the like.

According to yet another aspect of the present application, there is provided an non-aqueous based end-user composition comprising: (a) about 0.1 wt. % to about 40 wt. % of dehydroacetic acid (DHA) (b) about 0.1 wt. % to about 99.9 wt. % of at least one aprotic solvent, (ii) about 0.01 wt. % to about 5 wt. % of at least one antioxidant or radical quencher; (iii) about 0.5 wt. % to about 2.0 wt. % of polyvinyl pyrrolidone (PVP), and wherein the composition is stable, and capable of reducing yellowing of dehydroacetic acid.

Another important aspect of the present application provides an aqueous based end-user composition comprising: (i) preservative composition comprising: (a) about 0.1 wt. % to about 40 wt. % of dehydroacetic acid (DHA), (b) about 0.1 wt. % to about 99.9 wt. % of at least one aprotic solvent; (ii) about 0.01 wt. % to about 5 wt. % of at least one antioxidant or radical quencher; and (iii) about 0.01 wt. % to about 5 wt. % of at least one chelating agent or sequestering agent; (iv) about 0.5 wt. % to about 2.0 wt. % of polyvinyl pyrrolidone (PVP), and wherein the composition is stable, and capable of reducing yellowing of dehydroacetic acid.

BRIEF DESCRIPTION OF THE FIGURES

Further embodiments of the present invention can be understood with reference to the appended figures.

DETAILED DESCRIPTION OF THE INVENTION

Figure 1:
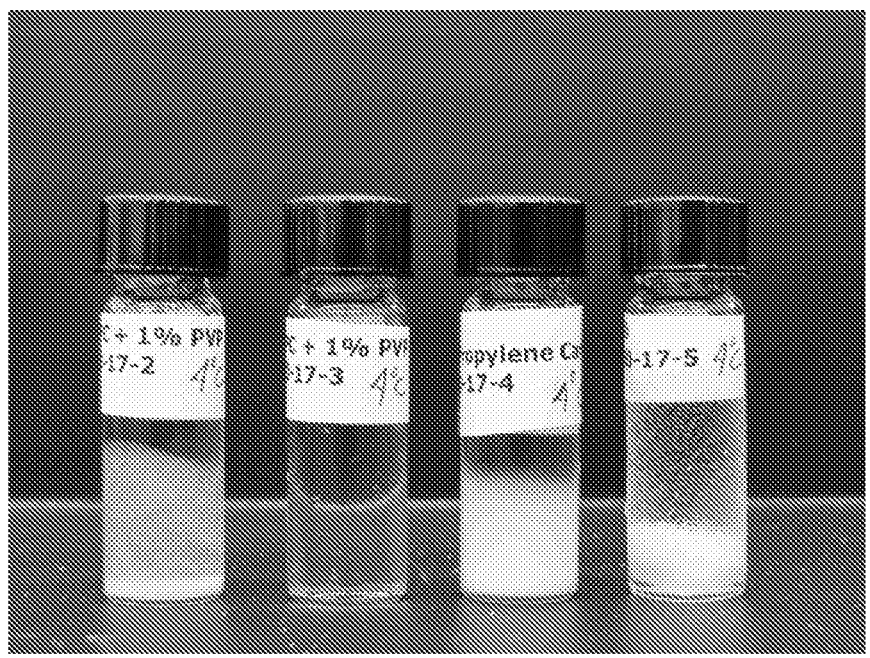
FIG. 1 shows freeze-thaw stability of propylene carbonate solution of DHA with or without PVP K-30 and K-90 conducted at −25° C.

While this specification concludes with claims particularly pointing out and distinctly claiming that which is regarded as the invention, it is anticipated that the invention can be more readily understood through reading the following detailed description of the invention and study of the included examples.

By the term "comprising" herein is meant that various optional, compatible components can be used in the compositions herein, provided that the important ingredients are present in the suitable form and concentrations. The term "comprising" thus encompasses and includes the more restrictive terms "consisting of" and "consisting essentially of" which can be used to characterize the essential ingredients such as preservatives, aprotic solvents, antioxidants, chelating agents, radical quenchers, and additives, if any, of the preservative composition.

All percentages, parts, proportions and ratios as used herein, are by weight of the total composition, unless otherwise specified. All such weights as they pertain to listed ingredients are based on the active level and, therefore; do not include solvents or by-products that may be included in commercially available materials, unless otherwise specified.

All references to singular characteristics or limitations of the present invention shall include the corresponding plural characteristic or limitation, and vice-versa, unless otherwise specified or clearly implied to the contrary by the context in which the reference is made.

Numerical ranges as used herein are intended to include every number and subset of numbers contained within that range, whether specifically disclosed or not. Further, these numerical ranges should be construed as providing support for a claim directed to any number or subset of numbers in that range.

As used herein, the words "preferred," "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

References herein to "one embodiment," "one aspect" or "one version" or "one objective" of the invention include one or more such embodiment, aspect, version or objective, unless the context clearly dictates otherwise.

All publications, articles, papers, patents, patent publications, and other references cited herein are hereby incorporated herein in their entireties for all purposes to the extent consistent with the disclosure herein.

The term "preservative" or "antimicrobial" as used herein is to be understood to refer to agents such as bactericides, fungicides, algicides, aquaticides, herbicide, insecticide, pesticide, plant growth regulators and the like, which are used for their ability to inhibit growth of and/or destroy biological and/or microbiological species such as bacteria, fungi, algae, caterpillar, insects, larvae, mildew, rodents, spider, worm and the like.

The term "non-yellowing" or "anti-yellowing" of dehydroacetic acid (DHA) is synonymously used in this application and it means that the preservative compositions comprising DHA do not turn yellow on storage or on heating, and do not yellow when they are added to the desired end-user products. Additionally, the term "slightly yellow" or "reduced-yellowing" means that the DHA of preservative composition turns to very slight yellow in color which is significantly lesser in yellowing intensity in comparison to that of DHA without propylene carbonate.

The term "sequestering agent" or "chelating agent" as used in this specification and claims relates to a compound which is capable of bonding or complexing a metal ion between two or more atoms of the compound, thereby neutralizing or controlling harmful effects of such metal ions, wherein holding or bonding of a metal ion is through, a combination of one or more different types of bonds including coordination and/or ionic bonds.

As used, herein, "stable" and "stability" refers to a composition which is significantly unaffected in chemical nature, physical homogeneity and/or color upon exposure to conditions reasonably expected to be incurred in transport, storage and their use in end-user applications. Stability may be determined either by empirical observation or by suitable methods of chemical and/or physical examination that would be known to one skilled in the art.

What is described herein is a stable and non-yellowing/reduced-yellowing synergistic preservative composition comprising: (i) about 0.1 wt. % to about 40 wt. % of dehydroacetic acid (DHA); and about 0.1 wt. % to about 99.9 wt. % of at least one aprotic solvent.

The preservative employed in a specific embodiment of the present application is commonly known as Dehydroacetic acid (DHA). The IUPAC name of DHA is 3-Acetyl-2-hydroxy-6-methyl-4H-pyran-4-one [CAS Registry Number is 520-45-6]. Additionally, an alternative embodiment of the present application contemplates to employ said DHA in the form of DHA, DHA salts, DHA isomers, DHA tautomers, or DHA derivatives which are known for a person skilled in the relevant art. The amount of DHA employed in the present application is in the range of from about 0.1 wt. % to about 5 wt. %, about 6 wt. % to about 10 wt. %, about 11 wt. % to about 15 wt. %, about 16 wt. % to about 20 wt. %, about 21 wt. % to about 25 wt. %, about 26 wt. % to about 30 wt. %, about 31 wt. % to about 35 wt. %, or about 36 wt. % to about 40 wt. %.

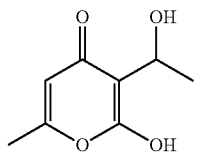

Dehydroaceic Acid (DHA)

A suitable aprotic solvent for the present application is selected from the group consisting of polar aprotic organic solvents, low polar aprotic solvents, and non-polar aprotic solvents, and wherein, the aprotic solvents can be water miscible, partially water miscible or poorly water miscible in nature. Aprotic solvents can include, but are not limited to, aliphatic and aryl ethers, cyclic ethers, $C_{1-20}$ alkanes substituted $C_{1-20}$ halo alkanes, $C_{1-20}$ halo alkanes, $C_{1-20}$ nitro alkanes, halo-benzenes, $C_{1-20}$ dialkylamides, cyclo-alkyl-pyrrolidones, $C_{1-20}$ cyclic amides, $C_{1-20}$ alkyl acetates, phenyl acetates, phenyl benzoates, $C_{1-20}$ alkyl acetates, $C_{1-20}$ esters of myristic acid, $C_{1-20}$ esters of lactic acid, $C_{1-20}$ alkylene carbonates, $C_{1-20}$ ketones, lactones, dialkyl sulfoxide, $C_{1-20}$ dialkyl amides of formic acid, $C_{1-20}$ nitriles, $C_{1-20}$ alkyl benzoates, $C_{1-20}$ dialkyl isosorbides, $C_{1-20}$ alkyl ortho/meta/para toluates alone or in combinations thereof.

According to another embodiment, the aprotic solvent is selected from the group including, but not limited to, perfluorohexane, α-α-α-trifluorotoluene, pentane, hexane, cyclohexane, methylcyclohexane, decalin, dioxane, carbon tetrachloride, freon-11, toluene, triethyl amine, carbon disulfide, dimethyl ether, diisopropyl ether, diethyl ether (ether), t-butyl methyl ether (MTBE), chloroform, ethyl acetate, 1,2-dimethoxyethane (GLYME), 2-methoxyethyl ether (DIGLYME), tetrahydrofuran (THF), methylene chloride, pyridine (Py), 2-butanone (MEK), acetone, hexamethylphosphoramide, N-methylpyrrolidinone, 2-pyrrolidone, N-methyl-2-pyrrolidone (NMP), n-ethyl-2-pyrrolidone, N-cyclohexyl-2-pyrrolidone, nitromethane, dimethylformamide (DMF), dimethyl aceta mide, acetonitrile, sulfolane, dimethyl sulfoxide (DMSO), decylmethylsulfoxide, ethylene carbonate, propylene carbonate, 4-methyl-1,3-diololan-2-one, butylene carbonate, caprolactam (cyclic amide), ester-caprolactone, ethyl acetate, methyl acetate, isopropyl myristate, ethyl oleate, methyl lactate, ethyl lactate, benzyl benzoate, dimethyl-iso-sorbide (DMI), butyrolactone alone or in combination thereof. An important embodiment of the present application employs at least one alkylene carbonate as the aprotic solvent.

Another non-limiting embodiment of the present application discloses that suitable aprotic solvents for the present application should be non-polar or less polar and highly polarizable in nature. Accordingly, it has been found that the most suitable aprotic solvents include ethylene carbonate, propylene carbonate, butylene carbonate, dimethylisosorbide (DMI), or 4,5-dimethyl-1,3,-dioxolan-2-one or their mixtures.

In accordance with another embodiment of the present application, the amount of aprotic solvent employed in the present application can range from about 0.1 wt. % to about 10 wt. %, about 11 wt. % to about 20 wt. %, about 21 wt. % to about 30 wt. %, about 31 wt. % to about 40 wt. %, about 41 wt. % to about 50 wt. %, about 51 wt. % to about 60 wt. %, about 61 wt. % to about 70 wt. %, about 71 wt. % to about 80 wt. %, about 81 wt. % to about 90 wt. %, about 91 wt. % to about 99.9 wt. %.

In another embodiment of the present application, the preservative composition comprising DHA and at least one aprotic solvent is capable of inhibiting or killing *Candida tropicalis, Candida albicans, Hansenula anomala, Saccharomyces cerevisiae, Torulaspora delbreuckii, Zygosaccharomyces bailii, Zygosaccharomyces rouxii, Bacillus subtilis, Bacillus cereus, Staphylococcus aureus, Staphylococus epidermidis, Escherichia coli, Salmonella typhimurium, Salmonella enteritidis, Pseudomonas aeruginosa, Aspergillus niger, Aspergillus flavus, Penicillium islandicum, Penicillium citrinum, Penicillium chrysogenum, Fusarium oxysporum, Fusarium graminearum, Fusarium solani, Alternaria alternata, Aspergillus brasiliensis, Burkhodelia cepacia, Enterobacter aerogenes, Enterobacter cloacae, Enterobacter gergoviae, Klebsiella pneumoniae, Proteus vulgaris, Pseudomonas fluorescens, Pseudomonas putida, Penicillium pinophilum* and/or *Mucor racemosus*.

Another embodiment of the present application provides a synergistic preservative composition of DHA, particularly in combination with desired aprotic solvents, and wherein, the DHA is solubilized in the aprotic solvents. The contribution of synergism by aprotic solvents allows employing significantly lesser amount of DHA than required without the combination of such aprotic solvents. Therefore, the lesser amount of DHA employed is capable of generating lower yellow intensity when employed in end-user products. Accordingly, the preservative composition comprising DHA and at least one aprotic solvent is capable of providing synergistic antimicrobial activity against bacterial and fungal strains. Some non-limiting bacterial and fungal strains for which significant synergistic action was demonstrated include *E. coli, S. aureus*, and *A. brasilensisi*. The ratio between DHA and aprotic solvent employed to provide synergistic activity can range from about 0.1 to 2: about 2 to 10, about 0.5 to 1.5: about 2.5 to 7.5, or about 1: about 5.

According to one important embodiment of the present application, the preservative composition is capable of providing a stable composition, wherein the DHA does not undergo discoloration at room/ambient temperature, at 50° C. on storage and during transit conditions. Particularly the DHA does not undergo yellow coloration at room/ambient temperature and at 50° C. on storage and transit conditions. Moreover, the preservative composition is stable on storage for at least 2 years at room/ambient temperature.

One specific embodiment discloses that preservative composition comprising DHA and at least one aprotic solvent is capable of preventing formation of major impurities of DHA generated due to hydrolysis if they are associated with protic solvents. Such impurities are responsible for the discoloration or yellowing of DHA. Therefore, addition of DHA into desired end-user products tends to cause yellow coloration. Further, during hydrolysis of DHA, many unique chromophores are formed as their major impurities and are sensitive to UV-Visible light and capable of absorbing UV radiation to yield certain colors. Also, it is possible that chromophores of major impurities can form color producing hydrogen-bonded complexes with phenolic and ketonic species when they are present in end-user application.

The major impurities with unique chromoporic structure include 1-(2,4-dihydroxy-3-methylphenyl)acetone, 2,5-dimethyl-7-hydroxy chromone, 3,5-dihydroxy toluene, 3,5-dimethyl phenol, 2,4,6-hepatnetrione, 2-acetyl-4,5-dimethyl phenol, 2,6-dimethyl-4H-pyran-4-one, 3,3,5-trimethyl-2-cyclohexen-1-one, 2,6-dimethyl-4H-pyran-4-one, 2-acetyl-4, 5-dimethyl phenol, 4,5,7-trimethyl coumarin, 2,4-dimethyl-7-hydroxy chromone, 3,5-dimethyl phenol, and/or 3,3,5-trimethyl-2-cyclohexen-1-one. Further, the amount of impurities formed varies depends on their (i) temperature—room, ambient or heat at 50° C. aged for 1 to 4 weeks of duration, (ii) pure DHA, 1% to 5% aqueous NaOH solution, and (iii) percentage quantity of DHA employed. Such yellow color generating impurities having chromophoric structure can be controlled or eliminated by employing the right antioxidants, radical quenchers and metal sequestering agents as described in the present application. According to another embodiment, the preservative composition of the present application can be incorporated into aqueous based or non-aqueous based products, and wherein, the aqueous or non-aqueous based compositions can be emulsions, microemulsion, solution, dispersion, suspension, complex coacervate, spray or concentrates.

A non-limiting embodiment of the present application employs wax based materials as a suspending agent or thickening agent for preparing DHA compositions comprising aprotic solvents, preferably propylene carbonate, wherein the wax component is capable of thickening the aprotic solvent or propylene carbonate medium and thereby allowing high % levels of DHA without having deposition during storage and transit. Such wax containing DHA dispersion compositions can be advantageously employed in various personal care and cosmetics based end-user applications to provide better results. The amount of DHA that can be dispersed in such compositions is from about 0.1 wt. % to about 60 wt. % of the total composition.

The preservative composition comprising DHA and at least one aprotic solvent can be employed in an aqueous and non-aqueous based end-user applications such as cosmetic products, toiletry products, personal care products, oral care products, skin care products, hair care products, household & cleaning products, Industrial and Institutional cleaning products, disinfecting products, contact lens, enzyme based formulations, wound care, sanitary products, agricultural compositions, textile industries, coating industries and/or laundry products.

According to one important embodiment of the present application, the conventional and non-conventional preservatives or preservative system can be employed as an additional preservatives in combination with aprotic solution of DHA to get broad spectrum preservatives, wherein the non-limiting list of conventional and non-conventional preservative include but not limited to parabens, (methyl, ethyl, propyl, butyl, etc), chlorophenisin, benzyl alcohol, organic acids such as sorbic, benzoic, salysilic and their salts, potassium sorbate, sodium benzoate, phenoxyethanol, diazolidinyl urea, imidazolidinyl urea, sodium hydroxymethyl glycinate, Hydantoins (DMDMH), sodium pyrithione, capryl glycol, phenyl ethanol, phenyl propanol, ethyl hexyl glycerine, benzyl alcohol, triclosan, 2-methyl-4-isothiazolin-3-one (MIT), 1,2-benzisothiazolin-3-one (BIT), 5-chloro-2-methyl-4-isothiazolin-3-one (CMIT), 2-octyl-4-isothiazolin-3-one (OIT), 3-iodo-2-propynylbutyl-carbamate (IPBC), zinc pyrithione (ZnPy), quaternary ammonium compounds and the like. The amount of conventional and non-conventional preservatives can be in the range of from about 0.1 wt. % to about 30 wt. % and alternatively based on the restricted use level of the individual components, and also include other possible ranges of such biocide or preservatives for the present application is from about 0.1 wt. % to about 5 wt. %, about 6 wt. % to about 10 wt. %, about 11 wt. % to about 15 wt. %, about 16 wt. % to about 20 wt. %, about 21 wt. % to about 25 wt. %, about 26 wt. % to about 30 wt. %.

Still another embodiment of the present application discloses that the amount of preservative composition employed in various aqueous and non-aqueous based end-user products/compositions is in the range of from about 0.01 wt. % to about 5.0 wt. % of the total composition. However, the other possible range of compositions to be employed in various end-user application can include but limited to about 0.01 wt. % to about 0.1 wt. %, about 0.1 wt. % to about 0.5 wt. %, about 0.6 wt. % to about 1.0 wt. %, about 1.1 wt. % to about 1.5 wt. %, about 1.6 wt. % to about 2.0 wt. %, about 2.1 wt. % to about 2.5 wt. %, about 2.6 wt. % to about 3.0 wt. %, about 3.1 wt. % to about 3.5 wt. %, about 3.6 wt. % to about 4.0 wt. %, about 4.1 wt. % to about 4.5 wt. %, or about 4.6 wt. % to about 5.0 wt. %, One specific embodiment of the present application provides a non-aqueous based end-user composition comprising: (a) about 0.1 wt. % to about 40 wt. % of dehydroacetic acid (DHA) (b) about 0.1 wt. % to about 99.9 wt. % of at least one aprotic solvent, (ii) about 0.01 wt. % to about 5 wt. % of at least one antioxidant or radical quencher, (iii) about 0.5 wt. % to about 2.0 wt. % of polyvinyl pyrrolidone (PVP), and wherein the composition is stable, and capable of reducing yellowing of dehydroacetic acid.

Another non-limiting embodiment of the present application employs at least one antioxidant agent for preparing a non-aqueous based end-user composition comprising phenols, hindered phenols, alkylated monophenols, alkylthiomethylphenols, hydroquinones and alkylated hydroquinones, tocopherols, hydroxylated thiodiphenyl ethers, alkylidenebisphenols, O-, N- and S-benzyl compounds, hydroxybenzylated malonates, aromatic hydroxybenzyl compounds, triazine compounds, benzylphosphonates, acylaminophenols, esters, hindered esters, tertiary butyl alcohol (TBA), benzofuranones, hydroxylamines, β-carotenes, natural antioxidants, antioxidants isolated from herbs, herbal extracts, and/or aminic antioxidants, and wherein the antioxidant agent employed to prepare non-aqueous based end-user compositions is capable of being soluble or miscible in non-aqueous medium of the composition.

Yet another embodiment of the present application provides a method for reducing yellowing of dehydroacetic acid (DHA) present in non-aqueous based end-user compositions comprising adding homogenous mixture of (a) about 0.1 wt. % to 99.9 wt. % of at least one aprotic solvents, (b) 0.01 wt. % to 40.0 wt. % dehydroacetic acid (DHA), and (c) about 0.1 wt. % to about 5 wt. % of at least one anti-oxidant, (c) about 0.5 wt. % to about 2.0 wt. % of polyvinyl pyrrolidone (PVP), and wherein, the non-aqueous based end-user composition may include cosmetic products, toiletry products, personal care products, oral care products, skin care products, hair care products, household & cleaning products, Industrial and Institutional cleaning products, disinfecting products, contact lens, enzyme based formulations, wound care, sanitary products, agricultural compositions, textile industries, coating industries and laundry products.

Still another embodiment of the present application provides an aqueous based end-user composition comprising: (i) preservative composition comprising: (a) about 0.1 wt. % to about 40 wt. % of dehydroacetic acid (DHA), (b) about 0.1 wt. % to about 99.9 wt. % of at least one aprotic solvent; (ii) about 0.01 wt. % to about 5 wt. % of at least one antioxidant; and (iii) about 0.01 wt. % to about 5 wt. % of at least one chelating agent or sequestering agent, (iv) about 0.5 wt. % to about 2.0 wt. % of polyvinyl pyrrolidone (PVP), and wherein the composition is stable, and capable of reducing yellowing of dehydroacetic acid.

The present application discloses a method for reducing yellowing of dehydroacetic acid (DHA) present in aqueous based end-user compositions comprising adding homogenous mixture of (a) about 0.1 wt. % to 99.9 wt. % of at least one aprotic solvent, (b) 0.1 wt. % to 40.0 wt. % dehydroacetic acid (DHA), (c) 0.01 wt. % to about 5 wt. % of at least one aqueous soluble anti-oxidant, and (d) 0.01 wt. % to about 5 wt. % of at least one chelating agent or sequestering agents, (e) about 0.5 wt. % to about 2.0 wt. % of polyvinyl pyrrolidone (PVP), and wherein, the pH of the aqueous based end-user composition is in the range of from about 3.5 to about 8.5, and other suitable range of pH can include about 3.5 to about 4.0, about 4.1 to about 4.5, about 4.6 to about 5.0, about 5.1 to about 5.5, about 5.6 to about 6.0, about 6.1 to about 6.5, about 6.6 to about 7.0, about 7.1 to about 7.5, about 7.6 to about 8.0.

Suitable chelating or sequestering agents for aqueous based end-user composition of the present application include polyols, gluconates, sorbitals, mannitols, carbonates, hydroxamates, catechols, α-amino carboxylates, alkanolamines, metal-ion sequestrants, hydroxy-carboxylic acids, aminocarboxylic acids, amino polycarboxylic acids, polyamines, polyphosphates, phosphonic acids, crown ethers, amino acids, polycarboxylic acids, cyclodextrin, phosphonates, polyacrylates, polymeric polycarboxylates, condensed phosphates, Ethylene-diamine-tetra acetic acid (EDTA), Glutamic acid diacetic acid (GLDA), a GLDA salt, a GLDA derivative, a tetrasodium or ammonium salt of GLDA, Methylglycine diacetic acid (MGDA), S,S-ethylenediaminedisuccinic acid (EDDS), Ethylene diamine-N,N'-disuccinic acid, or alkali or alkaline earth salts, Trisodium ethylene diamine-N,N-disuccinate (EDDS), (S,S)-Iminodisuccinic acid, (S,R)-Imino-disuccinic acid, hydroxyiminodisuccinic acid (HIDS), Trisodium methylglycine-N,Ndiacetate, Cysteic acid-N,N-diacetic acid, Cysteic acid-N-monoacetic acid, Alanine-N-monoacetic acid, β-Alanine-N,N-diacetic acid, (S)-α-Alanine-N,N-diacetic acid, N-[2-(3-Hydroxysuccinyl)]-L-serine, Methyliminodiacetic acid and their alkali metal salts, (S)-Aspartic acid-monoacetic acid, (S)-Aspartic acid-N,N-diacetic acid, (S)-Aspartic acid-monopropionic acid, N-(3-Hydroxysuccinyl)-aspartic acid, (S)-2-Sulfomethylaspartic acid, (S)-2-Sulfoethylaspartic acid, (S)-Glutamic acid-N,N-diacetic acid, (S)-2-Sulfomethylglutamic acid, (S)-2-Sulfoethylglutamic acid, (S)-Serine-N,N-diacetic acid, (S)-Phenylalanine-N,N-diacetic acid and alkali metal salts, Polyamino disuccinic acids, N-bis-[2-(1,2-Dicarboxyethoxy)ethyl]glycine (BCA6), N-bis-[2-(1,2-Dicarboxyethoxy)ethyl]aspartic acid (BCA5), N-bis-[2-(1,2-Dicarboxyethoxy)ethyl]-methylglycine (MCBA5), N-tris-[(1,2-Dicarboxyethoxy)ethyl]amine (TCA6), N-Methyliminodiacetic acid (MIDA), Iminodiacetic acid (IDA), N-(2-Acetamido)iminodiacetic acid (ADA), Hydroxymethyl-iminodiacetic acid, 2-(2-Carboxyethylamino)succinic acid (CEAA), 2-(2-Carboxymethylamino) succinic acid (CMAA), Diethylenetriamine-N,N'''-disuccinic acid, Triethylenetetramine-N,N'''-disuccinic acid, 1,6-Hexamethylenediamine-N,N'-disuccinic acid, Tetraethylenepentamine-N,N''''-disuccinic acid, 2-Hydroxypropylene-1,3-diamine-N,N'-disuccinic acid, 1,2-Propylenediamine-N,N'-disuccinic acid, 1,3-Propylenediamine-N,N'-disuccinic acid, cis-Cyclohexanediamine-N,N'-disuccinic acid, trans-Cyclohexanediamine-N,N'-disuccinic acid, Ethylene-bis-(oxyethylenenitrilo)-N,N'-disuccinic acid, Glucoheptanoic acid, ferrous lactate, ferrous bisglycinate, ferrous citrate, ferrous acetate, ferrous fumarate, ferrous succinate, ferrous sacchrate, ferrous tartarate, ferrous glycine sulfate, ferrous glutamate, ferrous gluconate, ferrous ascorbate, ferrous polymaltose, trimethyl citrate/citric acid, zinc citrate/citric acid alone or in combination. The addition of desired amount of chelating agents not only reduces the yellowing of DHA but it can also bring in synergy to the DHA composition, and thus reduces the quantity of DHA required to provide desired preservation.

The aqueous based end-user composition comprises (i) preservative composition comprising: (a) about 0.1 wt. % to about 40 wt. % of dehydroacetic acid (DHA), (b) about 0.1 wt. % to about 99.9 wt. % of at least one aprotic solvent; (ii) about 0.01 wt. % to about 5 wt. % of at least one antioxidant; (iii) about 0.01 wt. % to about 5 wt. % of at least one chelating agent or sequestering agent; (iv) about 0.5 wt. % to about 2.0 wt. % of polyvinyl pyrrolidone (PVP). Non-limiting examples of end-user applications or compositions include cosmetic products, toiletry products, personal care products, oral care products, skin care products, hair care products, household & cleaning products, Industrial and Institutional cleaning products, disinfecting products, contact lens, enzyme based formulations, wound care, sanitary products, agricultural compositions, textile industries, coating industries and laundry products.

Suitable antioxidants or radical quenchers for the aqueous based end-user composition comprises anti-oxidant agents and/or radical quenching agents that are soluble in aqueous medium and can be selected from the group consisting of phenols, hindered phenols, alkylated monophenols, alkylthiomethylphenols, hydroquinones and alkylated hydroquinones, tocopherols, hydroxylated thiodiphenyl ethers, alkylidenebisphenols, O-, N- and S-benzyl compounds, hydroxybenzylated malonates, aromatic hydroxybenzyl compounds, triazine compounds, benzylphosphonates, acylaminophenols, esters, hindered esters, tertiary butyl alcohol (TBA), benzofuranones, hydroxylamines, β-carotenes and/or aminic antioxidants.

According to one embodiment of the present application there is provided a process for preparing a non-aqueous based end-user composition comprising preparing a solution of: (i) about 0.1 wt. % to about 40 wt. % of dehydroacetic acid (DHA); (ii) about 0.1 wt. % to about 99.9 wt. % of at least one aprotic solvent; (iii) 0.01 wt. % to about 5.0 wt. % of at least one non-aqueous soluble or miscible anti-oxidant and/or radical quenching agent; and (iv) about 0.5 wt. % to about 2.0 wt. % of polyvinyl pyrrolidone (PVP).

According to another embodiment of the present application, a process for preparing an aqueous based end-user composition is provided which comprises preparing a solution of: (i) about 0.1 wt. % to about 40 wt. % of dehydroacetic acid (DHA); (ii) about 0.1 wt. % to about 99.9 wt. % of at least one aprotic solvent; (iii) about 0.01 wt. % to about 5.0 wt. % of at least one sequestering or chelating agent; (iv) 0.01 wt. % to about 5.0 wt. % of at least one aqueous soluble or miscible anti-oxidants; and (iv) about 0.5 wt. % to about 2.0 wt. % of polyvinyl pyrrolidone (PVP).

In an alternative embodiment of the present application, it is contemplated to incorporate the anti-oxidant and/or chelating agent to the end-user applications or compositions separately after adding a prescribed amount of the above described preservative composition, i.e. (i) about 0.1 wt. % to about 40 wt. % of dehydroacetic acid (DHA); and (ii) about 0.1 wt. % to about 99.9 wt. % of at least one aprotic solvent. Non-limiting end-user composition include cosmetic products, toiletry products, personal care products, oral care products, skin care products, hair care products, household & cleaning products, Industrial and Institutional cleaning products, disinfecting products, contact lens, enzyme based formulations, wound care, sanitary products, agricultural compositions, textile industries, coating industries and laundry products. Further, the pH range of end-user applications is generally in the range of from about 3.5 to about 8.5.

According to another embodiment of the present application, it is contemplated to incorporate separately a desired amount of antioxidant or chelating agent in various end-user products in an additional amount to reduce or eliminate the presence of yellowing of DHA if any, and wherein, such additional amount is incorporated after adding a preservative composition comprising (a) about 0.1 wt. % to about 40 wt. % of dehydroacetic acid (DHA), (b) about 0.1 wt. % to about 99.9 wt. % of at least one aprotic solvent; (ii) about 0.01 wt. % to about 5 wt. % of at least one antioxidant; (iii) about 0.01 wt. % to about 5 wt. % of at least one chelating agent or sequestering agent; and (iv) about 0.5 wt. % to about 2.0 wt. % of polyvinyl pyrrolidone (PVP).

In accordance with another embodiment of the present application a preservative composition is provided comprising polyvinyl pyrrolidone (PVP). Such composition is capable of withstanding heat and cold exposure, wherein the composition is stable for at least two years at room temperature or stable for at least 5 freeze/thaw cycles when the temperature is cycled from 50° C. to −24° C. in every 24 hours or stable for at least 4 weeks at about 50° C. Incorporation of PVP prevents formation of precipitation after it returns to room temperature during the process of freeze-thaw cycle. PVP of different commercial grades can be employed, including, but not limited to PVP K-30, PVP K-90, PVP K120 and the like. The percentage levels of PVP incorporated is in the range of from about 0.1 wt. % to about 2 wt. % of the total composition.

Further, certain aspects of the present invention are illustrated in detail by way of the following examples. The examples are given herein for illustration of the invention and are not intended to be limiting thereof.

EXAMPLE 1

Evaluation of Preservative System with Additives

In order to establish the influence of additives in association with DHA, several experiments were conducted and it was found additives like Chelating agents, Radical quenchers, Antioxidants, Radical quenchers and Binders like PVP make the preservative system more efficient either by incorporating in the preservative system or by adding to the end product.

TABLE 1

Yellowing Index Measurement of DHA

| S. No. | Sample | Δb (Yellowing Index) |
|---|---|---|
| 1. | Control | −1.63 |
| 2. | 1600 ppm DHA with no propylene carbonate | 15.7 |
| 3. | 1600 ppm DHA solubilized in propylene carbonate | 7.6 |
| 4. | 0.2% Trisodium EDTA/1600 ppm DHA solubilized in propylene carbonate | 6.7 |
| 5. | 0.2% Disodium EDTA/1600 ppm DHA solubilized in propylene carbonate | 4.2 |

Yellowing index measured by Hunter color meter demonstrated that there is clear benefit of solubilizing DHA in Propylene carbonate (PC) over DHA without Propylene carbonate. Further, it was observed that the addition of chelating agents such as trisodium EDTA and disodium EDTA capable of reducing or slowing down the yellowing of DHA as compared to that of propylene carbonate solution of DHA.

EXAMPLE 2

Preservative Efficacy Test (PET)

PET (Preservative Efficacy test) and Stability study were conducted in 5 different end-user products showed good significant results and synergy for propylene carbonate solution of DHA, the samples would include (i) Commercial Night Cream, (ii) Prolipid Lamelar Compostion (iii) Stemness Youth Serum, (iv) Standard Screening Emulsion, and (v) Baby Wipes Juice. The detailed composition of these end-user products comprising DHA solubilized Propylene Carbonate is described below in detail. The results of PET are provided in Table 1a and which clearly demonstrates the difference in employing various quantity of stabilized DHA and powdered DHA and their ability to kill bacteria, fungi or yeast.

TABLE 1a

Preservative Efficacy Test in various End-user Products

| S. No. | Contents | Commercial Consumer Products | Results Bacteria | Fungi | Yeast |
|---|---|---|---|---|---|
| 1. | 1600 ppm stabilized DHA formulation | Lamellar prolipid | Pass | Pass | Pass |
| 2. | 800 ppm of stabilized DHA with 800 ppm benzoic acid and 500 ppm 1,3-propanediol | formulation | Pass | Pass | Pass |
| 3. | 800 ppm of stabilized DHA | Baby Wipe juice | Not Tested | Pass | Pass |
| 4. | 1600 ppm of stabilized DHA | Sunscreen emulsion | Pass | Fail | Pass |
| 5. | 800 ppm of stabilized DHA | Night cream | Pass | Pass | Pass |
| 6. | 1200 ppm of stabilized DHA | | Pass | Pass | Pass |
| 7. | 1200 ppm of DHA powder added | | Fail | Fail | Fail |
| 8. | 400 ppm of stabilized DHA with 1.5% Hexanediol | Sternness youth serum | Pass | Fail | Fail |
| 9. | 1% DHA with Phenoxyethanol and benzoic acid | Standard screening emulsion | Pass | Pas | Pass |

EXAMPLE 3

Commercial Night Cream Composition Comprising Propylene Carbonate Solution of DHA

| INCI NAME | Ingredients | % W/W |
|---|---|---|
| Phase A oil phase | Cetearcy alcohol | 3.00 |
| | PEG-40 Stearate | 0.80 |
| | Caprylic/Capric Triglyceride | 2.50 |
| | 99.95% Ethylhexyl Methoxycinnamate + 0.05% BHT | 3.00 |

| INCI NAME | Ingredients | % W/W |
|---|---|---|
| | Glyceryl Stearate | 2.60 |
| | Dicaprylyl carbonate | 2.50 |
| | Dimethicone | 0.35 |
| | C12-15 Alkyl Benzoate | 2.50 |
| | Butyl Methoxy dibezoylmethane | 1.00 |
| Phase B thickener | Cyclomethicone | 2.15 |
| | Carbopol 980 | 0.10 |
| Phase C water phase | 80% Aqua + 20% Trisodium EDTA | 1.00 |
| | Aqua | 66.70 |
| | Glycerin | 7.00 |
| | Preservative | 1.5 |
| Phase D neutralization | 55% Aqua + 55% Sodium hydroxide | 0.05 |
| Total | | 100 |

| INCI NAME | Ingredients | % W/W |
|---|---|---|
| | Glycerin | 5.00 |
| Phase B | Glyceryl Stearate (and) Behenyl Alcohol (and) Palmitic Acid (and) Stearic Acid (and) Lecithin (and) Lauryl Alcohol (and) Myristyl Alcohol (and) Cetyl Alcohol | 4.50 |
| | Myristyl Myristate (and) | 4.00 |
| | Myristyl Laurate | 2.00 |
| | Dimethicone | 3.00 |
| | Glyceral Dilaurate | 1.00 |
| Phase C | Vital-ET | 1.50 |
| | Triethanolamine 99% | 0.15 |
| Phase D | Preservative | 1.75 |
| Total | | 100 |

EXAMPLE 4

Prolipid Lamelar Composition Comprising Propylene Carbonate Solution of DHA

| INCI NAME | Ingredients | % W/W |
|---|---|---|
| Phase A | Water | 75.25 |
| | Disodium EDTA | 0.05 |
| | Triethanolamine 99% | 0.05 |
| | 2-Propenic Acid, polymer with 1-ethylenyl-2-pyrolidinone and 3-(2-propenyloxy)-2,2-bis(2-propenyloxy)methyl)-1-propanol | 0.50 |

EXAMPLE 4A

Shampoo Composition Comprising Propylene Carbonete Solution of DHA

| Ingredients | % w/w |
|---|---|
| Water | 75.41 |
| Cocamidopropyl Betaine (46.4%) | 6.50 |
| Sodium Laureth Sulfate (70%) | 13.00 |
| $C_{12-15}$ Alkyl lactate | 1.00 |
| Citric Acid (25% aqueous solution) | 0.09 |
| Sodium Chloride (25% aqueous solution) | 4.00 |

TABLE 1b

Preservative Efficacy Test in Lamellar Prolipid formulation

| Treatment | Microorganisms | Days 2 | 7 | 14 | 21 | 28 | 35 |
|---|---|---|---|---|---|---|---|
| unpreserved control | S. aureus | 1.70E+06 | 6.60E+04 | 5.00E+01 | <10 | 2.50E+05 | Not Tested |
| | Bacterial Mixture | 1.20E+06 | 6.40E+05 | 1.10E+06 | >1.0E+06 | >1.0E+06 | Not Tested |
| | Mold Mixture | 2.10E+05 | 2.10E+05 | 1.50E+05 | 3.60E+05 | 3.50E+05 | Not Tested |
| 560 ppm stabilized DHA | S. aureus | 1.20E+06 | 6.90E+03 | 1.80E+02 | <10 | 2.00E+04 | Not Tested |
| | Bacterial Mixture | 6.00E+03 | 2.30E+05 | 3.90E+04 | 7.00E+01 | 4.60E+05 | Not Tested |
| | Mold Mixture | 2.20E+04 | 1.30E+03 | 6.20E+03 | 3.80E+03 | 3.50E+04 | Not Tested |
| 0.5% octanediol | S. aureus | 4.00E+01 | <10 | <10 | <10 | <10 | Not Tested |
| | Bacterial Mixture | <10 | <10 | <10 | <10 | <10 | Not Tested |
| | Mold Mixture | 2.10E+04 | 1.80E+04 | 4.40E+03 | 4.30E+03 | 5.00E+04 | Not Tested |
| 560 ppm stabilized DHA + 0.5% Octanediol | S. aureus | <10 | <10 | <10 | <10 | <10 | Not Tested |
| | Bacterial Mixture | <10 | <10 | <10 | <10 | <10 | Not Tested |
| | Mold Mixture | 3.4E3 | <10 | <10 | <10 | 3.0E2 | <10* |

Efficacy test is performed on 35th day if any recovery is seen on re-inoculation carried out after 28 days.

TABLE 1c

Preservative Efficacy Test in Shampoo Composition

| Treatment | Microorganisms | Days 2 | 7 | 14 | 21 | 28 | 35 |
|---|---|---|---|---|---|---|---|
| unpreserved control | Bacterial Mixture | 1.00E+07 | 1.00E+07 | 1.00E+05 | 1.00E+07 | 1.00E+07 | 1.00E+07 |
| | Candida albicans | 1.00E+03 | 1.00E+04 | 1.00E+04 | 1.00E+04 | 1.00E+04 | 1.00E+04 |
| | Aspergillus niger | 1.00E+02 | 1.00E+02 | 1.00E+02 | 1.00E+02 | 1.00E+02 | NT |

TABLE 1c-continued

Preservative Efficacy Test in Shampoo Composition

| Treatment | Microorganisms | Days | | | | | |
|---|---|---|---|---|---|---|---|
| | | 2 | 7 | 14 | 21 | 28 | 35 |
| 1600 ppm stabilized DHA | Bacterial Mixture | 1.00E+01 | <10 | <10 | <10 | <10 | <10 |
| | Candida albicans | <10 | <10 | <10 | <10 | <10 | <10 |
| | Aspergillus niger | <10 | <10 | <10 | <10 | <10 | <10 |
| 1600 DHA Powder | Bacterial Mixture | 1.00E+07 | 1.00E+04 | 1.00E+05 | 1.00E+05 | 1.00E+07 | 1.00E+07 |
| | Candida albicans | <10 | <10 | <10 | <10 | <10 | <10 |
| | Aspergillus niger | <10 | <10 | <10 | <10 | <10 | <10 |

Efficacy test is performed on $35^{th}$ day if any recovery is seen on re-inoculation carried out after 28 days

EXAMPLE 5

Stemness Youth Serum Composition Comprising Propylene Carbonate Solution of DHA

| INCI NAME | Ingredients | % W/W |
|---|---|---|
| Phase A | Water | 72.00 |
| | Acrylates/C10-30 Alkyl Acrylate Crosspolymer | 0.30 |
| Phase B | Diisopropyl Adipate | 2.00 |
| | Isodecyl Neopentanoate | 4.00 |
| | Glyceryl Stearate (and) Laureth-23 | 1.00 |
| | Ceteareth-20 | 2.00 |
| | Refined Shea Butter | 1.50 |
| Phase C | TEA | 0.20 |
| | Water | 5.00 |
| Phase D | Cyclopentasiloxane (and) Dimethicone/Vinyltrimethylsiloxysilicate Crosspolymer | 3.00 |
| | Glycerin (and) Glyceryl Polyacrylate | 2.00 |
| | Cyclopentasiloxane (and) Dimethiconol | 2.00 |
| | Water (and) Butylene Glycol (and) Pentapeptide | 3.00 |
| | BPD 500 (Kobo) | 0.50 |
| | Preservative | 1.50 |
| | Total | 100 |

EXAMPLE 6

Standard Screening Emulsion Composition Comprising Propylene Carbonate Solution of DHA

| INCI NAME | Ingredients | % W/W |
|---|---|---|
| Phase A | Stearic acid, NF | 5 |
| | Mineral Oil | 2.5 |
| | Cetyl Alcohol, NF | 1 |
| | Ceteareth-5 | 0.5 |
| | PEG 100 Stearate | 1.5 |
| Phase B | DI water | 86.9 |
| | Triethanolamine 99% | 1 |
| Phase C | Preservative | 1 |
| Phase D | Citric Acid 30% aq. | 0.6 |
| | Total | 100 |

EXAMPLE 7

Baby Wipe Juice Composition Comprising Propylene Carbonate Solution of DHA

| INCI NAME | Ingredients | % W/W |
|---|---|---|
| Phase A | DI Water | 97.9 |
| | Citric Acid 10% aq. | 0.5 |
| Phase B | Tween 20 (Liposorb 20) | 0.2 |
| | Vitamin E (Vital ET) | 0.05 |
| | Fragrance (Petal Avalanch) | 0.05 |
| Phase C | Si Tec DMC 6031 | 0.1 |
| | Glycerine | 0.5 |
| Phase D | NaOH 10% aq. (adjust pH) | 0.2 |
| | Preservative | 0.5 |
| | Total | 100 |

EXAMPLE 8

Method of Preparation for Solution of DHA in PC

The dehydroacetic acid (DHA) and propylene carbonate (PC) are mixed together in a beaker with magnetic stirrer and then at least one appropriate additives such as Glutamic acid, N,N-Diacetic acid, tetra sodium salt (GL-PD-S), Butylated Hydroxy Toluene (BHT), Tertiary butanol (TBA) are added to form a homogenous solution comprising DHA, PC and at least one additive, and wherein, the pH of these formulation vary from about 6 to about 7. The various formulations are disclosed in Table 2.

TABLE 2

Experimental compositions with additives:

| Ingredients | Experiment batches | | | | | | |
|---|---|---|---|---|---|---|---|
| | 202-1 | 202-2 | 202-3 | 202-4 | 202-5 | 202-6 | 202-7 |
| Dehydroacetic acid (DHA) | — | 8 | 8 | 8 | 8 | 8 | 8 |

TABLE 2-continued

Experimental compositions with additives:

| Ingredients | 202-1 | 202-2 | 202-3 | 202-4 | 202-5 | 202-6 | 202-7 |
|---|---|---|---|---|---|---|---|
| Propylene carbonate | 100 | 91.8 | 91.8 | 91.9 | 91.6 | 92 | 91.6 |
| Glutamic acid, N,N-diacetic acid, tetra sodium salt (GL-PD-S) | — | — | — | 0.1 | — | — | — |
| Butylated Hydroxy Toluene (BHT) | — | 0.2 | — | — | 0.4 | — | — |
| Tertiary butanol (TBA) | — | — | 0.2 | — | — | — | 0.4 |
| Total | 100 | 100 | 100 | 100 | 100 | 100 | 100 |
| pH | ~7.0 | 6.05 | 6.24 | 6.14 | 6.28 | 6.25 | 6.22 |

EXAMPLE 9

Stability Study of the Preservative Systems

Table 3 of the present application demonstrates the color stability of the preservative samples that are described in Example 8 and Table 2 observed over one month.

TABLE 3

Color stability test of preservative compositions of example 8

| Sample ref.# | Start date | Initial Gardner # | 1 week 40° C. | 1 week 50° C. | 2 week 40° C. | 2 week 50° C. | 3 week 40° C. | 3 week 50° C. | 4 week 40° C. | 4 week 50° C. |
|---|---|---|---|---|---|---|---|---|---|---|
| 202-1 | May 2, 2014 | 0 | 0 | 0 | 0 | 0 | 0 | 0 | 0 | 0 |
| 202-2 | May 2, 2014 | 2 | 2 | 2 | 3 | 4 | 3 | 4 | 3 | 4 |
| 202-3 | May 2, 2014 | 2 | 2 | 2 | 3 | 4 | 3 | 4 | 3 | 4 |
| 202-4 | May 2, 2014 | 2 | 2 | 2 | 3 | 4 | 3 | 4 | 3 | 4 |
| 202-5 | May 2, 2014 | 2 | 2 | 2 | 3 | 4 | 3 | 4 | 3 | 4 |
| 202-6 | May 2, 2014 | 2 | 2 | 2 | 3 | 4 | 3 | 4 | 3 | 4 |
| 202-7 | May 2, 2014 | 2 | 2 | 2 | 3 | 4 | 3 | 4 | 3 | 4 |
| 202-8 | May 2, 2014 | 2 | 2 | 2 | 3 | 4 | 3 | 4 | 3 | 4 |

EXAMPLE 10

Quantification of DHA in Experimental Formulations

The DHA quantifications studies were conducted through HPLC method which demonstrates that the preservative systems are stable even after heat-aging at 50° C. for 1 month. The corresponding HPLC results are showed in Table 4.

TABLE 4

HPLC results for the quantification of DHA in compositions of example 8

| Sample Ref. # | DHA with/without Additives | DHA active at Room temperature | DHA active at 50° C. |
|---|---|---|---|
| 12475-202-1 | 0% active | Not Detected | Not Detected |
| 12475-202-2 | 8% DHA + 0.2% BHT | 8.2% | 8.1% |
| 12475-202-3 | 8% DHA + 0.2% Tertiary butanol | 7.8% | 7.8% |
| 12475-202-4 | 8% DHA + 0.1 GLPD-S % | 8.1% | 8.1% |
| 12475-202-5 | 8% DHA + 0.4% BHT | 8.1% | 8.1% |
| 12475-202-6 | 8% DHA | 8.2% | 7.8% |
| 12475-202-7 | 8% DHA + 0.4% Tertiary butanol | 8.1% | 8.1% |

EXAMPLE 11

Quantification of DHA in Bay Wipe Juice, an End-User Product

The Table 5 shows that additives like PC, chelating agents and radical quenchers help in retaining DHA level more as compared to the sample without additives even after heat-aging at 50° C. for 1 month.

TABLE 5

HPLC results for the quantification of DHA in Baby wipe juice

| Sample Ref. # | DHA with/without Additives | Calculated DHA | DHA in Room Temp Stability (in ppm) | DHA in 50° C. Stability (in ppm) |
|---|---|---|---|---|
| 12475-247-1 | 2% of (8% DHA in PC) | 0.16% | 1554 | 967 |
| 12475-247-2 | 0.16% of DHA Powder | 0.16% | 946 | 749 |
| 12475-247-3 | 2% of (8% DHA in PC) + 0.2% of EDTA | 0.16% | 1659 | 1080 |
| 12475-247-5 | 2% of (8% DHA in PC) + 0.2% of t-butanol | 0.16% | 1638 | 1089 |
| 12475-247-8 | Control | 0.00% | Not Detected | Not Detected |

EXAMPLE 12

Freeze Thaw Stability Studies

Freeze thaw stability study was conducted to evaluate the stability of preservative compositions, and during the process of evaluation, a tiny amount of precipitate was observed after the sample returns to room temp. This precipitate took longer time to go back in the solution. To resolve this issue several antifreeze products were tried and PVP (Polyvinyl pyrrolidone) was found to be effective in improving the freeze-thaw process and thaw time of these compositions.

Freeze thaw experiment was conducted for the composition comprising propylene carbonate and DHA with or without PVP at 4° C. It was observed that the use of PVP K-30 (in sample #12580-17-2) and K-90 (in sample #12580-17-3) were very helpful in freeze-thaw stability. Particularly, PVP K-90 demonstrated faster thaw time within 10 to 15 minutes in comparison to that of K-30 in returning to its normal condition at room temperature. Similar observations were recorded for the compositions at −25° C.

Further, the comparison study of 1% PVP K-90 with lower percentages of from about 0.1% to about 0.7% was performed to optimize the level of PVP K-90. It was observed that 0.7% K-90 found to have improved stability over other concentrations in freeze-thaw experiment conducted at 4° C., however, the 0.7% K-90 concentration was not enough for freeze-thaw conditions of −25° C., and therefore, the compositions at −25° C. took very longer time to return to its normal state, i.e. approximately 24 hrs. The 1% K-90 concentration found to be very optimum % for freeze-thaw experiment conducted at −25° C.

Figure 2:
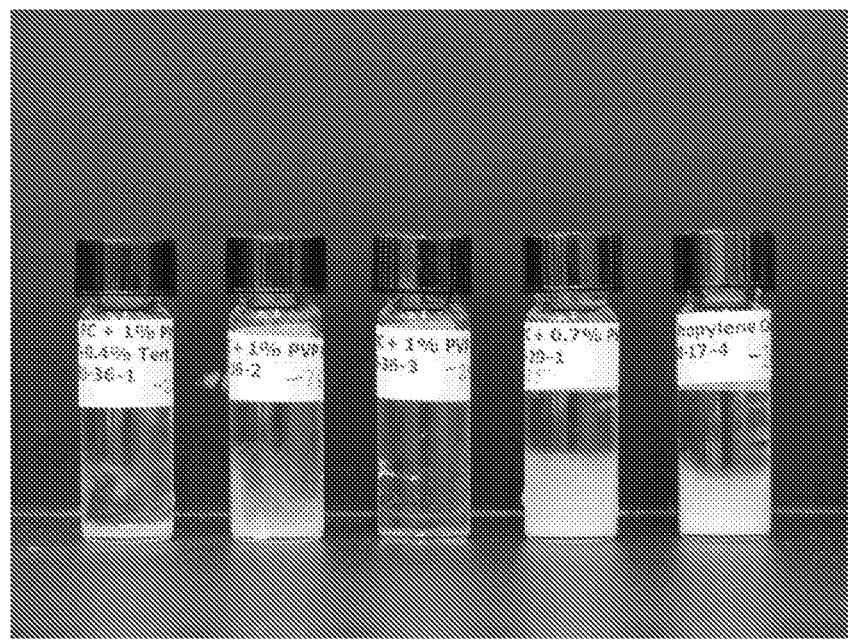
FIG. 2 shows comparative freeze-thaw stability study of propylene carbonate solution of DHA having 0.7% K-90 and 1% K-90 conducted at −25° C.

From the above detailed experiments and FIGS. 1 and 2, it is clearly demonstrated that 1% PVP K-90 is the best for freeze-thaw stability studies conducted at both 4° C. and −25° C.

Moreover, the comparison study of the preservative composition systems with 1% PVP K-90, with and without additives, with and without PVP is in progress, additionally, similar type of experiments for 1% PVP K-120 with and without additives, with and without PVP was evaluated and found to be better than PVP K-120.

EXAMPLE 13

Preservative Composition (8% DHA in PC) Comprising PVP

The preservative composition is prepared by mixing 8% of DHA in propylene carbonate to form a solution, and then required amount of PVP of particular grade is added into the solution to form homogenous system for further evaluation. The various compositions are disclosed in detail in Table 6.

TABLE 6

Composition comprising DHA (8%) in PC and PVP

| Ingredients | K-90 (36-1) | K-120 (36-2) | K-90 (36-3) (in %) | Control (without PVP) (17-4) | K90 (29-1) |
|---|---|---|---|---|---|
| DHA | 8 | 8 | 8 | 8 | 8 |
| Propylene carbonate | 90.2 | 91 | 91 | 92 | 91.3 |
| PVP | 1 | 1 | 1 | — | 0.7 |
| BHT | 0.4 | — | — | — | — |
| Tertiary butanol | 0.4 | — | — | — | — |
| Total | 100 | 100 | 100 | 100 | 100 |
| pH | 6.42 | 6.47 | 6.18 | 6.33 | 6.2 |
| Gardner color # | 1 | 1 | 1 | 1 | 1 |

EXAMPLE 14

Synergism Activity of Propylene Carbonate and DHA Against Antimicrobial Agents

The synergism of two-component compositions is demonstrated by testing a wide range of concentrations and ratios of compounds as follows:

Tryptic Soy Broth (TSB) media was used for bacterial evaluations and Yeast Malt Broth (YMB) for fungal evaluations. The compounds DHA or the aprotic solvents were added to the media and serially diluted. After serially diluting the media, 100 µl of a suspension of the testing bacteria or fungi were added to a final concentration of approximately 106 −5 CFU/ml. The inoculated media was then incubated at 32° C. for 2-5 days for bacteria or at 28° C. for 3-7 days for fungi.

The lowest concentration of each compound or mixtures to inhibit visible growth was taken as the minimum inhibitory concentration (MIC). The MIC's were taken as end points of activity. End points for the mixtures of compound A (DHA) and compound B (aprotic solvent) were then compare with the end points for the pure active ingredient alone.

Synergism was determined by a commonly used and accepted method described by Kull A. C.; Eisman, P. C.; Sylwestrowicz, H. D. and Mayer, R. L. 1961. Applied Microbiology, 9:538-541 using the ratio determine by:

$$Qa/QA + Qb/QB = \text{synergy}$$

Wherein:

QA is the concentration of compound A in PPM, acting alone, which produced and end point.

Qa is the concentration of compound A in PPM, in the mixture, which produced and end point.

QB is the concentration of compound B in PPM, acting alone, which produced and end point.

Qb is the concentration of compound B in PPM, in the mixture, which produced and end point.

When the sum of Qa/QA+Qb/QB is greater than one, antagonism is indicated. When the sum is equal to one additive is indicated, and when less than one synergism is demonstrated.

The results for demonstration of synergism between DHA and different aprotic solvents are shown in Table 7. The table shows: (1) Test organism (bacteria or fungi), (2) The end-point activity in PPM measured by MIC for the compound A alone (QA), for compound A in the mixture (Qa), for compound B alone (QB), for compound B in the mixture (Qb), (3) The ppm ratio of DHA (compound A) to Solvent (compound B) in that particular combination and the synergy index (SI) based on the formula SI=Qa/QA+Qb/QB.

Further, the synergistic effect of DHA is demonstrated from the result of Table 7a, and wherein, the various DHA stabilized compositions comprising aprotic solvents confirmed significant boosting effect of DHA against microbial organisms particularly against fungal strains. Moreover, it was observed that the viscosity of the compositions were within the range of desired levels which is essential for stability of the compositions, wherein the viscosity test is performed using Brookfield DVe RV TC spindle #93@10 rpm. The boosting or synergistic effect of 0.5% stabilized DHA on efficacy was seen for all combinations. The mixture or combination of 0.7% stabilized DHA with 1% Octanediol was found very efficacious even at higher pH~6.7 although DHA was not efficacious above pH 5.8

TABLE 7

Synergistic study of DHA with aprotic solvents against antimicrobial agents
Combination of DHA with solvent

| Microorganism | Solvent | DHA (A) (ppm) | DHA (a) (ppm) | Solvent (B) (ppm) | Solvent (b) (ppm) | Ratio A:B | SI |
|---|---|---|---|---|---|---|---|
| Bacteria: E. coli (ATCC 8739) | Propylene carbonate | 1250 | 625 | 6250 | 3125 | 1:5 | 1.0 |
| | Dimethyl isosorbide | 2500 | 1250 | 12500 | 3125 | 1:5 | 0.75 |
| S. aureus (ATCC 6538) | Propylene carbonate | 2500 | 625 | 12500 | 6250 | 1:5 | 0.75 |
| | Dimethyl isosorbide | 1250 | 625 | 12500 | 6250 | 1:10 | 1.0 |
| Fungi: A. brasilensts (ATCC 16404) | Propylene Carbonate | 78 | 10 | 6250 | 3125 | 1:80 | 0.63 |
| | Dimethyl Isosorbide | 39 | 20 | 3125 | 780 | 1:80 | 0.75 |

TABLE 7a

Viscosity of Sunscreen composition comprising stabilized DHA with aprotic solvents

| Formula/ NTBK # | Product Description | pH | Viscosity cP |
|---|---|---|---|
| 12580-178-1 | 0.5% stabilized DHA + 1.5% hexanediol | ~6.7 | 14500 |
| 12580-178-2 | 0.5% stabilized DHA + 1% octanediol | ~6.7 | 14700 |
| 12580-178-3 | 0.5% stabilized DHA + 0.5% Liquapar MEP | ~6.8 | 14500 |
| 12580-178-4 | 0.5% stabilized DHA | ~6.6 | 14200 |
| 12580-178-5 | 0.049% DHA powder | ~6.5 | 14400 |
| 12580-178-6 | 0.61% Optiphen ND | ~6.6 | 14000 |
| 12580-178-7 | 1.5% stabilized DHA | ~6.6 | 14200 |
| 12580-178-8 | 1.5% hexanediol | ~6.8 | 14500 |
| 12580-178-9 | 1% Octanediol | ~6.7 | 14700 |
| 12580-178-10 | 0.5% Liquapar MEP (paraben) | ~6.8 | 14800 |
| 12580-178-11 | Unpreserved | ~6.7 | 13800 |

The above table demonstrated synergistic effect of compositions comprising propylene carbonate and DHA against bacterial and fungal organisms.

EXAMPLE 15

Selection of Solvents for Preparing Non-Yellowing DHA Composition

In order to choose the suitable solvent for preparing non-yellowing DHA composition, the different possible protic, aprotic solvents were selected and evaluated individually and also as their suitable mixture.

In case of aprotic solvents, it was selected based on its compatibility with other ingredients present in the end-user products. Further, the regulatory requirement was also considered as an important element in choosing preferred aprotic solvent for preparing non-yellowing/reduced-yellowing DHA composition of the present application. The high content of DHA can be introduced in the solvent by dispersing or dissolving the DHA in their corresponding aprotic solvents. Moreover, it was determined that in some cases, the higher metal content in the end-user product increased the yellowing of DHA and accordingly, the solvents were selected for the present application. The various solvents selected are disclosed in Table 8.

TABLE 8

List of aprotic solvents evaluated for developing non-yellowing DHA composition

| Nature of solvents | % of DHA soluble | Comment | Yellowing at RT pH For 1 month | At 50° C. |
|---|---|---|---|---|
| Ethlyene carbonate | None | Solids | — — | — |
| Propylene carbonate | 8-10 | Liquid | — No yellowing | Slight yellowing after 4 week (2-3 Gardner color) |
| Butylene carbonate | 6 | Liquid | — No yellowing | Slight yellowing (2-3) after 4 weeks |
| Mixture of ethylene, propylene, butylene carbonates | 8 | Liquid | — No yellowing | Slight yellowing after 5 week (2-3) |
| Mixture of ethylene propylene carbonate | 9-11 | Liquid | — No yellowing | Slightly yellow after 5 week(2) |
| Dimethyl isosorbide (DMI) | 8-10 | Liquid | — Slight yellow after 3 weeks | Slight to medium yellowing (3-4) |
| Dimethyl formamide (DMF) | 6-8 | Liquid | — Slight yellow after 3 weeks | Slight to medium yellowing (3-4) |
| Cyclohexane | 3-5 | Liquid | No yellowing | Slight yellowing (2-3) |
| N-Methyl pyrrolidone (NMP) | 6-8 | Liquid | — Slight yellowing after 3 week | Slight to medium yellowing (4-5) |
| Bees wax | 7-9 | Liquid | — No yellowing | Slight yellowing (2-3) |
| Medium polar mineral oil | 8-10 | Liquid | — No yellow | Slight to medium yellowing (3-4) |
| Methyl lactate | 7-9 | Liquid | — No yellow | Slight to medium yellowing (3-4) |
| Isopropyl Myristate | 6-8 | Liquid | — Slight yellowing after 4 week | Slight to medium yellowing (4-5) |

Further, the applicants have evaluated various protic solvents to understand their ability to render non-yellowing/reduced-yellowing DHA composition for employing in various end-user products that are aqueous in nature.

The yellowing of DHA in protic solvents depended on its solubility therein, and wherein, the strong yellowing was noted from about pH 5 to pH 7 and then yellowing decrease in asymptotic manner at low and high pH. The yellowing of DHA increased drastically when aprotic aromatic compounds were present along with DHA due to radical coupling between DHA and such solvents comprising aromatic compounds. The protic solvents evaluated are listed in Table 9. Many esters were also evaluated, and it was found that these esters demonstrated very low solubility in many solvents, and strong yellowing in many solvents where solubility was relatively good.

Further, it was experimentally demonstrated that the mechanism of yellowing by exposing the end-user products to light and heat for a desired period of time. The decomposition of DHA was low at room temperature (RT) and at high temperature, wherein, the small amount of DHA decompose to form a radical and couple by themselves to form traces high of epsilon chromophoric products and if aromatic aprotic solvents are present along with DHA in solution they couple to form a longer chromophore with high intensity yellow color in water. Our detailed chromophoric product evaluation indicated that the coupled products were same irrespective of heat or light that causes yellowing, however, the concentration of the chromophore impurity varied according to exposure levels of heat or light.

TABLE 9

List of protic polar solvents evaluated as solvents for DHA composition

| Nature of solvents | % of DHA soluble | Comments | Yellowing at RT pH For 1 month | At 50° C. |
|---|---|---|---|---|
| Water | 0.05 | — | 4 No yellowing | Slight to medium yellowing in 4-5 weeks |
| Water | 1.0 | — | 5 Medium yellowing in 2 week | Medium yellowing in 5-6 weeks |
| Water | 6 | — | 6.5 Medium yellowing in 1 week | Strong yellowing in 8-11 weeks |
| Water | 20 | Crystallize | 8 Slight yellowing | Slight to medium in 4-5 weeks |
| 1,3 propanediol | 2 | — | — Slight yellowing in 1 week | Strong yellowing in 7-9 weeks |
| Phenethylpropanol | 8 | Crystallize | — yellow on day one | Strong yellowing in 9-11 weeks |
| Phenethyl ethanol | 8 | — | — Yellow on day one | Strong yellowing in 8-10 weeks |
| Pentylene glycol | 0.9 | — | — Yellow in day 2 | Strong yellowing in 8-10 weeks |
| 1,2hexanediol | 0.9 | — | — Yellow in 9 days | Strong yellowing in 8-10 weeks |

TABLE 9-continued

List of protic polar solvents evaluated as solvents for DHA composition

| Nature of solvents | % of DHA soluble | Comments | pH | Yellowing at RT For 1 month | At 50° C. |
|---|---|---|---|---|---|
| Capryl glycol | 2.5% | — | — | Yellow in 30 days | Medium to strong yellowing in 6-8 weeks |
| Phenoxy ethanol | 8 | — | — | Yellow in day 1 | Strong yellowing in 10-11 weeks |

EXAMPLE 16

Dispersion of 60% DHA in Propylene Carbonate

| Ingredients | wt. % |
|---|---|
| Propylene carbonate | 30 |
| Tertiary butanol | 0.4 |
| BHT | 0.4 |
| DHA | 60.0 |
| Tixogel | 0.5 |
| Bees wax | 3.0 |
| Ceruba wax | 3.0 |
| Lanolin wax | 2.7 |

EXAMPLE 17

Dispersion of 50% DHA in Propylene Carbonate

| Ingredients | wt. % |
|---|---|
| Propylene carbonate | 40.0 |
| DHA | 50.0 |
| Tertiary butanol | 0.4 |
| BHT | 0.4 |
| Tixogel | 0.6 |
| Beeswax | 3.0 |
| Jojba oil | 2.5 |
| Lanolin wax | 3.1 |

EXAMPLE 18

Evaluation of Yellowing in Consumer Products

Various commercially available consumer products were subjected to evaluation to find their ability to withstand at 50° C. on one month storage. From the Table 10, it was clear that the consumer products demonstrated maximum yellowing between pH 5.5 to 7.0 and decreased drastically with increase or decrease in pH. Further, the yellowing increased with increase in water content present in the consumer compositions and solubilization of DHA in such water content of said consumer compositions.

TABLE 10

Study of yellowing effects in consumers products

| Consumer product tested (DHA in PC system) | pH | Quantity (ppm) | Yellowing observation 1 month Heat-age at 50° C. | Δb (Difference in yellow color for control and product after heat aging |
|---|---|---|---|---|
| Night Cream | ~6.0 | 1600 | No yellowing | <3.0 |
| Prolipid | 5.5 | 1600 | No yellowing | <3.0 |
| Sun Screen emulsion | 5.5 | 1600 | No yellowing | <3.0 |
| Stemness youth serum | 5.0 | 1600 | No yellowing | <3.0 |
| Non-ionic emulsion | 5.6 | 800 | No yellowing | <3.0 |
| Prolipid 1 | 5.7 | 800 | No yellowing | <3.0 |
| Baby wipe juice | 5.4 | 800 | Yellow | >3.0 |
| Standard Screening emulsion | 6.0 | 1600 | Yellow | >3.0 |
| Gel cream | 6.0 | 800 | Yellow | >3.0 |

TABLE 10a

Study of yellowing effects in consumers products

| S. No. | Consumer products tested* | pH | DHA solution (in ppm) | Yellowing 1 month Heat-age | Δb* |
|---|---|---|---|---|---|
| 1. | Prolipid 141 formula | 5.5 | 1,600 | No yellowing at 40 C. | 0-3 |
| 2. | Sun Screen emulsion | 5.5 | 1,600 | No yellowing at 40 C. | 0-3 |
| 3. | Stemness youth serum | 5.4 | 400 | No yellowing at 40 C. | 0-3 |
| 4. | Non-ionic emulsion (In-House) | 5.6 | 800 | No yellowing at 45 C. | 0-3 |
| 5. | Prolipid formula (In-House) | 5.7 | 800 | No yellowing at 45 C. | 0-3 |
| 6. | Leave in conditioner | 4.6 | 400 | No yellowing at 40 C. | 0-3 |
| 7. | Natrosol 250 HHR CS Hair spray | 4.9 | 800 | Slight yellowing at 40 C. | 3-4 |
| 8. | Sulfate free shampoo | 5.3 | 1200 | Slight yellowing at 40 C. | 3-4 |
| 9. | Standard Screening emulsion | 6.0 | 800 | Slight Yellowing at 40 C. | 3-4 |
| 10. | Gel cream(In-house) | 6.0 | 800 | Yellowing at 45 C. | 5.0 |

*The composition # 202-5 of Table 2 is used for testing consumer products.

EXAMPLE 19

Rheological Measurement for Skin Care Emulsions

Figure 3:
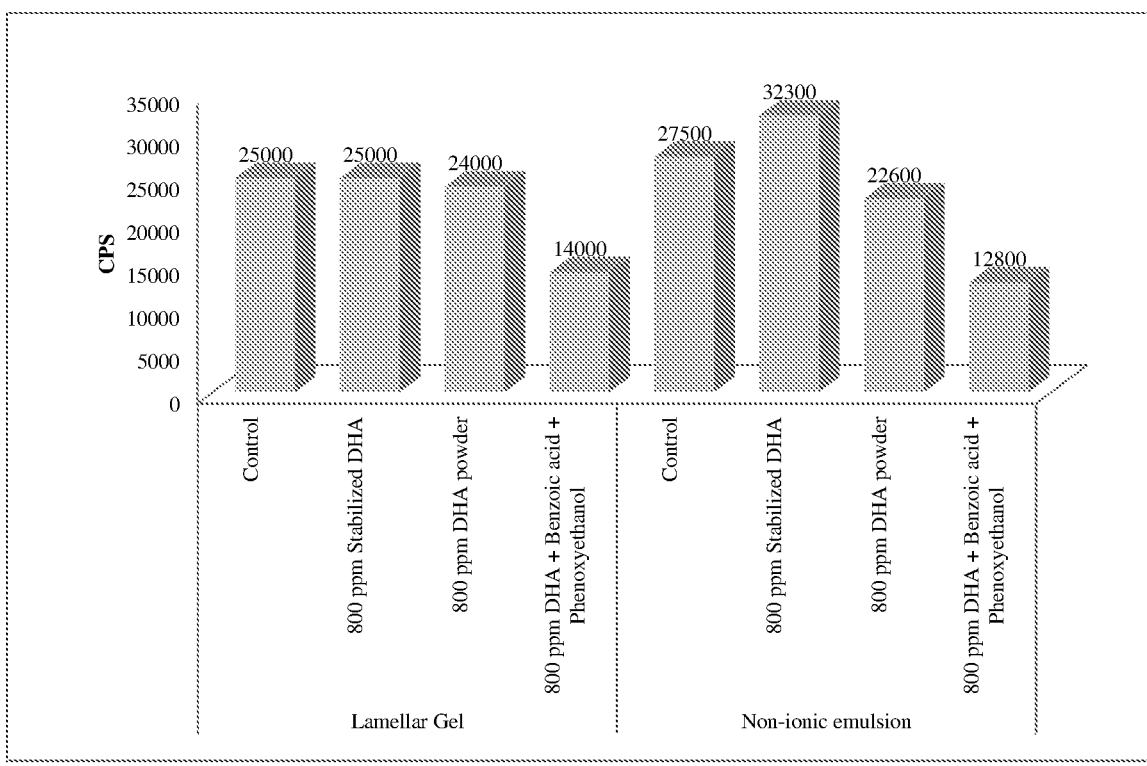
FIG. 3 shows reological stability of stabilized DHA in lamellar gel and non-ionic emulsion composition.

Rheological testing is designed to determine the viscosity of a skin care emulsion using a Brookfield viscometer. The rheological experiments were performed in lamellar gel and non-ionic emulsion based compositions. It was demonstrated that stabilized DHA of the present application is capable of maintaining the viscosity compositions at par with control readings and whereas, the viscosity measurements were significantly decreased for the mixture comprising DHA, benzoic acid and Phenoxyethanol. The experimental results were duly presented in FIG. 3.

While this invention has been described in detail with reference to certain preferred embodiments, it should be appreciated that the present invention is not limited to those precise embodiments. Rather, in view of the present disclosure, many modifications and variations would present themselves to those skilled in the art without departing from the scope and spirit of this invention.

What is claimed is:

1. A stable and non-yellowing/reduced-yellowing synergistic preservative composition comprising:
   i. about 8.0 wt. % of dehydroacetic acid (DHA); and
   ii. about 92 wt. % of propylene carbonate (PC), wherein composition is delivered as emulsion, microemulsion, nanoemulsion, solution, dispersion, suspension, complex coacervate or concentrate,
   wherein said composition is capable of inhibiting or killing *Staphylococcus aureus, Escherichia coli, Aspergillus niger, Aspergillus brasiliensis* and *Candida albicans,*
   wherein the DHA does not undergo yellow coloration or undergoes reduced yellow coloration at room/ambient temperature and at 50° C. on storage and transit conditions, and
   wherein said composition is stable on storage of at least 2 years at room temperature.

2. The preservative composition according to claim 1, wherein said composition is aqueous or non-aqueous based.

3. The preservative composition according to claim 1, wherein said composition is employed in various aqueous and non-aqueous based end-user applications comprising cosmetic products, toiletry products, personal care products, oral care products, skin care products, hair care products, household & cleaning products, Industrial and Institutional cleaning products, disinfecting products, contact lens, enzyme based formulations, wound care, sanitary products, agricultural compositions, textile industries, coating industries and/or laundry products.

4. The preservative composition according to claim 1, wherein said composition comprises one or more additional biocides selected from the group consisting of triclosan, 2-methyl-4-isothiazolin-3-one (MIT), 1,2-Benzisothiazolin-3-one (BIT), 5-Chloro-2-methyl-4-isothiazolin-3-one (CMIT), 2-Octyl-4-isothiazolin-3-one (OIT), 3-iodo-2-propynylbutyl-carbamate (IPBC), 3-iodopropynyl-N-phenyl carbamate (IPPC), zinc pyrithione (ZnPy), bronopol, Quaternary ammonium compounds alkyl parabens, chlorophenisin, benzyl alcohol, organic acids, sorbic acid, benzoic acid, salicylic and their salts, potassium sorbate, sodium benzoate, phenoxyethanol, diazolidinyl urea, imidazolidinyl urea, sodium hydroxymethyl glycinate, Hydantoins, sodium pyrithione, capryl glycol, phenyl ethanol, phenyl propanol, ethyl hexyl glycerine, benzyl alcohol.

5. The preservative composition according to claim 1, wherein the amount of preservative composition employed in aqueous and non-aqueous based end-user products/compositions is in the range of from about 0.01 wt. % to about 5.0 wt. % of the total composition.

6. A non-aqueous based end-user composition comprising: i. about 0.01 wt. % to about 5.0 wt. % of the preservative composition of claim 1; ii. about 0.01 wt. % to about 5 wt. % of at least one antioxidant or radical quencher; and iii. about 0.5 to about 2.0 wt. % of polyvinyl pyrrolidone (PVP), wherein the composition is stable, and capable of reducing yellowing of dehydroacetic acid.

7. The non-aqueous based end-user composition according to claim 6, wherein said composition is employed in aqueous and non-aqueous based end-user applications comprising cosmetic products, toiletry products, personal care products, oral care products, skin care products, hair care products, household & cleaning products, Industrial and Institutional cleaning products, disinfecting products, contact lens, enzyme based formulations, wound care, sanitary products, agricultural compositions, textile industries, coating industries and laundry products.

8. The non-aqueous based end-user composition according to claim 6, wherein said anti-oxidant is selected from the group consisting of phenols, hindered phenols, alkylated monophenols, alkylthiomethylphenols, hydroquinones and alkylated hydroquinones, tocopherols, hydroxylated thiodiphenyl ethers, alkylidenebisphenols, O-, N- and S-benzyl compounds, hydroxybenzylated malonates, aromatic hydroxybenzyl compounds, triazine compounds, benzylphosphonates, acylaminophenols, esters, hindered esters, tertiary butyl alcohol (TBA), benzofuranones, hydroxylamines, β-carotenes, and/or aminic antioxidants.

9. The non-aqueous based end-user composition according to claim 6, wherein said anti-oxidant is added externally to said non-aqueous based end-user compositions having a pH of 4 to 8.

10. A method for reducing yellowing of dehydroacetic acid (DHA) present in a non-aqueous based end-user composition, wherein, the method comprises adding (a) about 0.01 wt. % to about 5.0 wt. % of a preservative composition of claim 1 (b) about 0.1 wt. % to about 5 wt. % of at least one anti-oxidant, to the non-aqueous based end user composition.

11. An aqueous based end-user composition comprising: i. about 0.01 wt. % to about 5.0 wt. % of the preservative composition of claim 1; ii. about 0.01 wt. % to about 5 wt. % of at least one antioxidant; iii. about 0.01 wt. % to about 5 wt. % of at least one chelating agent or sequestering agent; and iv. about 0.5 to about 2.0 wt. % of polyvinyl pyrrolidone (PVP), wherein the composition is stable, and capable of reducing yellowing of dehydroacetic acid.

12. The aqueous based end-user composition according to claim 11, wherein said composition is employed in cosmetic products, toiletry products, personal care products, oral care products, skin care products, hair care products, household & cleaning products, Industrial and Institutional cleaning products, disinfecting products, contact lens, enzyme based formulations, wound care, sanitary products, agricultural compositions, textile industries, coating industries and laundry products.

13. A method for reducing yellowing of dehydroacetic acid (DHA) present in an aqueous based end-user composition, wherein the method comprises adding (a) about 0.01 wt. % to about 5.0 wt. % of a preservative composition of claim 1, (b) 0.01 wt. % to about 5 wt. % of at least one aqueous soluble anti-oxidant, and (c) 0.01 wt. % to about 5 wt. % of at least one chelating agent or sequestering agent, to the non-aqueous based end-user composition.

14. The aqueous based end-user composition according to claim 11, wherein the pH of the aqueous composition is from about 3.5 to about 8.5.

15. The aqueous based end-user composition according to claim 11, wherein the chelating or sequestering agent is selected from the group consisting of polyols, gluconates, sorbitals, mannitols, carbonates, hydroxamates, catechols, α-amino carboxylates, alkanolamines, metal-ion sequestrants, hydroxy-carboxylic acids, aminocarboxylic acids, amino polycarboxylic acids, polyamines, polyphosphates, phosphonic acids, crown ethers, amino acids, polycarboxylic acids, cyclodextrin, phosphonates, polyacrylates, polymeric polycarboxylates, condensed phosphates, Ethylenediamine-tetra acetic acid (EDTA), Glutamic acid diacetic acid (GLDA), a GLDA salt, a GLDA derivative, a tetrasodium or ammonium salt of GLDA, Methylglycine diacetic acid (MGDA), S,S-ethylenediaminedisuccinic acid (EDDS), Ethylene diamine-N,N'-disuccinic acid, or alkali or alkaline earth salts, Trisodium ethylene diamine-N,N-disuccinate (EDDS), (S,S)-Iminodisuccinic acid, (S,R)-Imino-disuccinic acid, hydroxyiminodisuccinic acid (HIDS), Trisodium methylglycine-N,Ndiacetate, Cysteic acid-N,N-diacetic acid, Cysteic acid-N-monoacetic acid, Alanine-N-monoacetic acid, β-Alanine-N,N-diacetic acid, (S)-α-Alanine-N,N-diacetic acid, N-[2-(3-Hydroxysuccinyl)]-L-serine, Methyliminodiacetic acid and their alkali metal salts, (S)-Aspartic acid-monoacetic acid, (S)-Aspartic acid-N,N-diacetic acid, (S)-Aspartic acid-monopropionic acid, N-(3-Hydroxysuccinyl)-aspartic acid, (S)-2-Sulfomethylaspartic acid, (S)-2-Sulfoethylaspartic acid, (S)-Glutamic acid-N,N-diacetic acid, (S)-2-Sulfomethylglutamic acid, (S)-2-Sulfoethylglutamic acid, (S)-Serine-N,N-diacetic acid, (S)-Phenylalanine-N,N-diacetic acid and alkali metal salts, Polyamino disuccinic acids, N-bis-[2-(1,2-Dicarboxyethoxy)ethyl]glycine (BCA6), N-bis-[2-(1,2-Dicarboxyethoxy)ethyl]aspartic acid (BCA5), N-bis-[2-(1,2-Dicarboxyethoxy)ethyl]-methylglycine (MCBA5), N-tris-[(1,2-Dicarboxyethoxy)ethyl]amine (TCA6), N-Methyliminodiacetic acid (MIDA), Iminodiacetic acid (IDA), N-(2-Acetamido)iminodiacetic acid (ADA), Hydroxymethyl-iminodiacetic acid, 2-(2-Carboxyethylamino)succinic acid (CEAA), 2-(2-Carboxymethylamino)succinic acid (CMAA), Diethylenetriamine-N,N"-disuccinic acid, Triethylenetetramine-N,N'"-disuccinic acid, 1,6-Hexamethylenediamine-N,N'-disuccinic acid, Tetraethylenepentamine-N,N""-disuccinic acid, 2-Hydroxypropylene-1,3-diamine-N,N'-disuccinic acid, 1,2-Propylenediamine-N,N'-disuccinic acid, 1,3-Propylenediamine-N,N'-disuccinic acid, cis-Cyclohexanediamine-N,N'-disuccinic acid, trans-Cyclohexanediamine-N,N'-disuccinic acid, Ethylene-bis-(oxyethylenenitrilo)-N,N'-disuccinic acid, Glucoheptanoic acid, ferrous lactate, ferrous bisglycinate, ferrous citrate, ferrous acetate, ferrous fumarate, ferrous succinate, ferrous sacchrate, ferrous tartarate, ferrous glycine sulfate, ferrous glutamate, ferrous gluconate, ferrous ascorbate, ferrous polymaltose, alone or in combination.

16. The aqueous based end-user composition according to claim 11, wherein the anti-oxidant agent and/or radical quenching agent is selected from the group consisting of phenols, hindered phenols, alkylated monophenols, alkylthiomethylphenols, hydroquinones and alkylated hydroquinones, tocopherols, hydroxylated thiodiphenyl ethers, alkylidenebisphenols, O-, N- and S-benzyl compounds, hydroxybenzylated malonates, aromatic hydroxybenzyl compounds, triazine compounds, benzylphosphonates, acylaminophenols, esters, hindered esters, tertiary butyl alcohol (TBA), benzofuranones, hydroxylamines, β-carotenes and/or aminic antioxidants.

17. A process for preparing the preservative composition of claim 6 comprising preparing a solution of: i. about 8 wt. % dehydroacetic acid (DHA); ii. about 92 wt. % of propylene carbonate (PC); iii. 0.01 wt. % to about 5.0 wt. % of at least one non-aqueous soluble anti-oxidant and/or radical quenching agent; and iv. about 0.5 to about 2.0 wt. % of polyvinyl pyrrolidone (PVP).

18. A process for preparing the composition of claim 11 comprising preparing a solution of: i. about 8 wt. % of dehydroacetic acid (DHA); ii. about 92 wt. % of propylene carbonate (PC); iii. about 0.01 wt. % to about 5.0 wt. % of at least one sequestering or chelating agent; iv. 0.01 wt. % to about 5.0 wt. % of at least one aqueous soluble anti-oxidant; and v. about 0.5 wt. % to about 2.0 wt. % of polyvinyl pyrrolidone (PVP).

19. The composition according to claim 11, wherein said anti-oxidant and/or chelating agent is added externally to the aqueous based end-user composition having a pH of 4 to 8.

* * * * *